United States Patent [19]

Sundelin et al.

[11] 4,325,695
[45] Apr. 20, 1982

[54] DENTAL SALIVA EJECTOR

[76] Inventors: Bo Sundelin, 7, Södra Lundsgatan, 667 00 Forshaga; Bengt R. A. Wahlin, 8, Pejlingsgatan, 421 76 Västra Frölunda; B. Göran Johansson, 19, Sövdeborgsvägen, 275 00 Sjöbo, all of Sweden

[21] Appl. No.: 196,981

[22] Filed: Oct. 14, 1980

[30] Foreign Application Priority Data

Oct. 11, 1979 [SE] Sweden ............................... 7908449

[51] Int. Cl.³ ............................................. A61C 17/04
[52] U.S. Cl. ......................................... 433/91; 433/94
[58] Field of Search ............................. 433/91, 93, 94

[56] References Cited

U.S. PATENT DOCUMENTS

| 540,562 | 6/1895 | Simonson | 433/91 |
|---|---|---|---|
| 2,436,040 | 2/1948 | Friedman | 433/91 |
| 2,830,371 | 4/1958 | Dahl | 433/93 |
| 3,373,492 | 3/1968 | Batch | 433/91 |

Primary Examiner—Robert Peshock
Attorney, Agent, or Firm—William A. Drucker

[57] ABSTRACT

A dental saliva ejector has a perforated wall provided at each side of a suction opening to prevent tongue and muceous membranes of the patient to be sucked into the opening. The ejector further has a portion intended to rest against a front tooth of the mandible and a securing means intended to contact the chin such that the ejector is held in place by a clamping action between chain and front tooth to prevent pressure against the mouth bottom.

4 Claims, 4 Drawing Figures

DENTAL SALIVA EJECTOR

This invention refers to a dental saliva ejector.

Conventional dental saliva ejectors suffer from a number of serious drawbacks. One of these drawbacks is that the patient being treated often feels pain, mainly due to the fact that the saliva ejectors will press against pain sensitive areas in the mouth bottom by the existing methods for holding the ejector in place. Another drawback, which also results in discomfort to the patient, resides in the fact that the suction capacity often is unsatisfactory and, primarily, that the ejector is often stuck to the muceous membranes which can lead to pethechiale bleedings.

For the dentist and hygienist it is of course of importance that the suction capacity is such that she/he can operate under dry conditions, and further, that the operation area is as large as possible. The latter may only be achieved when the ejector besides from being a suction means, also forms a device to keep the tongue away and, when treating the buccal side of the teeth (the cheek side), keeps the cheek away.

The object of the invention has therefore been to eliminate said drawbacks and to provide a simple, inexpensive and efficient dental saliva ejector which does not cause discomfort to the patient but offers dentist and hygienist as perfect operation areas as possible.

To accomplish these and other objects the invention has the characteristics disclosed in the following claims.

The accompanying drawings illustrate two exemplifying embodiments of the invention.

Figure 1:
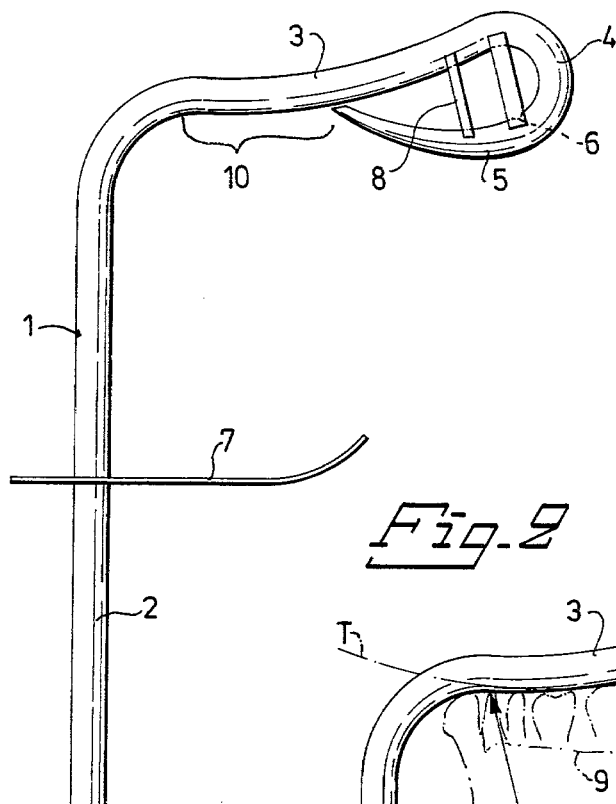
FIG. 1 is a front view of the new dental saliva ejector in a first embodiment.

The new dental saliva ejector comprises a substantially tubular member having the general reference numeral 1. In the embodiment shown, said member comprises a straight portion 2 which in the upper thereof merges into a curved portion 3, substantially following the teeth row (line T of FIG. 2). Said curved portion 3 continues via a curved transition 4, preferably with a definite radius, in a lower curved portion 5 directed towards the portion 3. Said lower portion is closed and flattened in the free end thereof. At least one suction opening 6 is provided in close proximity to the transition 4 in the upper wall of portion 5 but may also be provided in the transition portion itself. Said suction opening is covered on both sides by narrow plastic ribs 8 in order to prevent the tongue and muceous membranes of the patient from being inwardly sucked (stuck by suction action). As appears from FIG. 1 and FIG. 3 the suction opening 6 respectively 6' is effectively separated from the tongue and the muceous membranes by the portion 5, the portion 3, the transition 4 and the front and rear ribs 8 respectively 8'.

A securing member having the general reference numeral 7 is displaceably mounted relative to the straight portion 2. In the embodiments shown, said member comprises a relatively thin plate which in the right side, according to FIG. 1, is curved to fit the chin of the patient. The plate 7 has an opening of such a diameter that it surrounds the straight portion 2 with a slight clearance or play making it easily displaceable along said portion. The securing thereof is automatically obtained by means of the so called drawer-effect, i.e. a downwardly directed push on the portion of the plate which is most remote from the straight portion results in a turning movement locking the plate against displacement in relation to the straight portion. The free space 10 in FIG. 1 permits the ejector to be inserted into the mouth at various depths which makes the ejector applicable to mouths of different sizes.

The plate 7 as well as the tubular member 1 is preferably made from a relatively rigid plastic material as none of these members is to be deformed to any greater extent by the use. Also in this respect the new dental saliva ejector differs from conventional dental saliva ejectors which in general are to be deformed to fit the mouth of the patient.

Also as to the shape the tubular member 1 differs from the corresponding member of conventional dental saliva ejectors as it is bent in the opposite direction compared to these.

Figure 2:
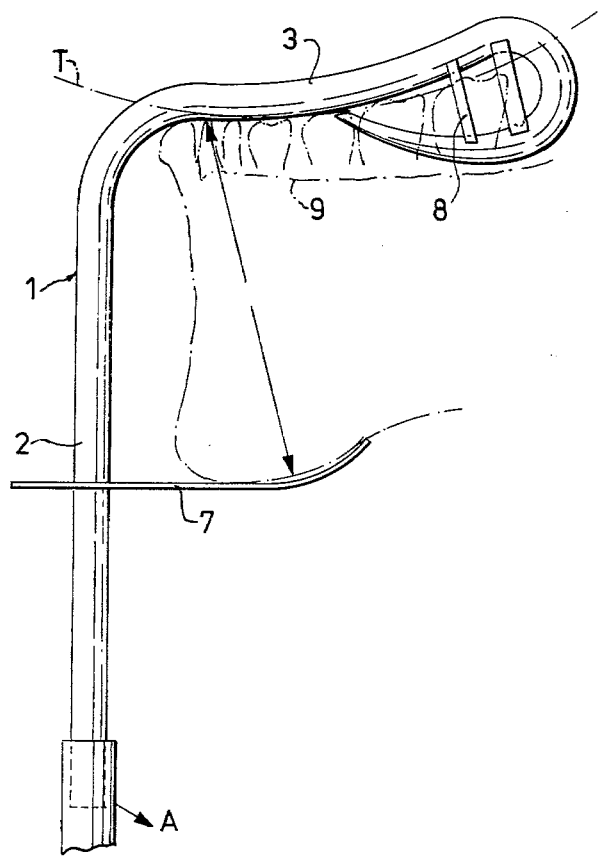
FIG. 2 is a similar view, shematically illustrating the location of the dental saliva ejector in the mouth of the patient.

FIG. 2 illustrates how the new dental saliva ejecto may eliminate the drawbacks mentioned in the preamble.

Thus the securing of the ejector in the mouth of the patient is not achieved by clamping the ejector between the mouth bottom and the chin as in most known saliva ejectors, but by clamping the ejector between one of the front teeth of the mandibles and the chin. As may be seen in FIG. 2 the engaging portion 3 of the dental saliva ejector will engage one of said front teeth at the same time as the securing member 7 engages a part of the patient's chin portion. Force and anti-force will therefore act according to the arrows of FIG. 2 and it is understood that a reliable and for the patient painless securing is thereby obtained. As the portion 3 substantially follows the teeth row in the height direction the saliva ejector becomes non-voluminous and thereby offers the dentist required space for the treatment. Furthermore, the tongue is effectively kept out of the way. A suction hose is connected to the straight portion 2 in a manner known per se and it may be mentioned that the load that the weight thereof makes, assists in releasing the pressure from sensitive areas in the mouth of the patient. Nowadays, as is well known, the patients are usually treated in an almost lying position and the hose and members associated therewith therefore tend to fall towards the chest of the patient, which gives rise to a force in the direction of the arrow A in FIG. 2 and said force tends to raise or lift that one of the portions 3 and 5 being most remote from the straight portion 2 and hereby these portions are prevented from falling down towards the mouth bottom, indicated by reference numeral 9.

The patients are, as mentioned, usually treated in a lying or semilying position and therefore, saliva and mucus will flow downwardly towards the pharynx and for this purpose, the suction opening or openings are preferably placed in connection to the transition 4. Because a wall portion (the lower portion of the straight portion 5) will always be located between the mouth bottom and the suction opening and as the portions 3 and 5 are positioned one above the other and are of substantially the same dimension and because the ribs 8 are bridging the portions 3 and 5 outside the opening, every risk for the device getting caught by suction against the mouth bottom or some adjacent portion will be effectively prevented. The tongue as well as the muceous membranes of the mouth are effectively held out of contact with the suction openings by means of the tiny plastic ribs 8 and further can not reach the operational field by means of said ribs. The new dental saliva ejector can not be catched by suction as may the ejectors presently on the market.

Of course the described saliva ejector may be shaped in a number of ways. Thus—the term 'tubular member' only defines that the member should be hollow so that a suction action may be achieved by the same. In case said member is made in an injection molding process, for example as to reversed parts, glued together, it is possible to provide a waist between the portions 3 and 5 and the portion 3 naturally needs not be straight and may optionally be fully eliminated. However, it is a clear advantage that the portion 3 is provided, as it gives the part of the tubular member reaching into the mouth such a straight and smooth design, that the dentist takes no risk to get hooked with some treating instrument.

The design of the tubular member as a rigid unit also offers the advantage that the dental saliva ejector further may be buccally used.

Figure 3:
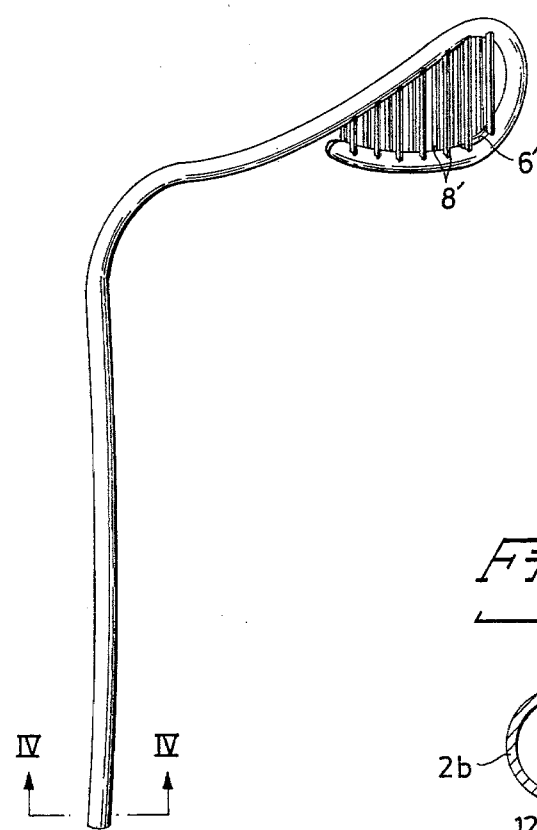
FIG. 3 is a perspective view of a second and preferred embodiment of the invention.

The shape of FIG. 3 has been proved to give the best results in most cases. According to this embodiment a plurality of thin, but relatively rigid ribs 8 are used. In practice the ribs are some thicker in the direction perpendicular to the plane of the drawing as in the plane of the drawing. Further, there is only one opening 6' which is rectangular in shape and extends over the distance between two of the ribs 8'. As the opening has a considerable area parts which have been able to pass between the ribs will also pass through the opening and the combination of the relatively big opening and the narrow passages between the ribs makes the saliva ejector extremely safe against the opening being blocked. The ribs serve as a screen. The size and location of the opening 6' further prevents the ejector from sucking air when used upon a patient in a lying or semilying position.

Figure 4:
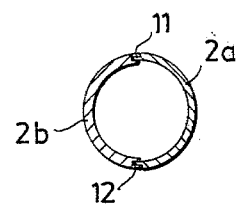
FIG. 4 is a section along line IV—IV of FIG. 3 on an enlarged scale.

The saliva ejector is preferably made in two reversed parts and as appears from FIG. 4 the parts—only 2a and 2b being shown—have interengaging portions 11,12 such that the two reversed parts may be pressed together and may then be sealed by a plastic welding method, said interengaging portions facilitating the sealing operation.

We claim:

1. A dental saliva ejector, comprising: a substantially tubular element having a straight part connected to a flexible hose or the like and extending outside the mouth of the patient and continuing in a suction part introduced in the mouth of a patient, said suction part having an upper portion substantially flowing in the active position of the ejector of the upper surface of the teeth of the mandible, and having a lower portion at the lower surface thereof provided to extend at least in part of its extension in close proximity to the mouth bottom of the patient, a suction opening in an upper surface of said lower and/or in the transition between said lower portion and said upper portion, a plurality of thin ribs bridging the distance between the upper and said lower portion, some of said ribs being located in a plane in front of a central plane through the section part and some of them behind said plane, said ribs being spaced and located to allow minor particles to pass between them and reach said suction opening but to prevent muceous membranes of the patient from coming in contact with said suction opening.

2. A dental saliva ejector as claimed in claim 1, wherein the suction opening is substantially rectangular in shape and extends over the distance between two of the ribs.

3. A dental saliva ejector as claimed in claim 1, further including a securing element wherein the straight part serves as a guide for said securing element brought into contact with the chin of the patient and being displaceable relative to said straight part and being lockable in any desired position along said straight part, the upper portion of the suction part having a surface provided to rest against one of the front teeth of the mandible of the patient such that the saliva ejector is held in place by means of interaction between the securing element pressed against the chin of the patient and said portion being pressed against one of the front teeth of the mandible, the suction portion having such an extension substantially perpendicular to said straight portion that the end thereof in the active position of the ejector will be located in the rearmost portion of the mouth.

4. A dental saliva ejector as claimed in claim 1, wherein the substantially tubular element comprises two substantially reversed parts of substantially semicircular section each made from a relatively rigid plastic material and each provided along the entire extension thereof with two spaced apart beads formed to provide a snap connection between said parts and further sealed generating walls.

* * * * *